(12) United States Patent
Gardella et al.

(10) Patent No.: US 11,166,490 B2
(45) Date of Patent: Nov. 9, 2021

(54) E-CIGARETTE VAPORIZER DEVICE FILLING SYSTEM AND METHOD

(71) Applicant: Portland Engineering, Inc., Central Point, OR (US)

(72) Inventors: Christopher A. Gardella, Tigard, OR (US); Justin Levi Rettger, West Linn, OR (US)

(*) Notice: Subject to any disclaimer, the term of this patent is extended or adjusted under 35 U.S.C. 154(b) by 15 days.

(21) Appl. No.: 16/682,770

(22) Filed: Nov. 13, 2019

(65) Prior Publication Data
US 2021/0137173 A1    May 13, 2021

(51) Int. Cl.
*A24F 40/10*    (2020.01)

(52) U.S. Cl.
CPC ....... *A24F 40/10* (2020.01); *A61M 2209/045* (2013.01)

(58) Field of Classification Search
None
See application file for complete search history.

(56) References Cited

U.S. PATENT DOCUMENTS

| | | | |
|---|---|---|---|
| 6,637,430 B1 * | 10/2003 | Voges | A61M 15/0065 128/200.14 |
| 7,010,900 B2 | 3/2006 | Grossman et al. | |
| 7,497,237 B2 | 3/2009 | Till | |
| 9,247,773 B2 | 2/2016 | Memari et al. | |
| 9,320,301 B2 | 4/2016 | Memari et al. | |
| 9,668,522 B2 | 6/2017 | Memari et al. | |
| 9,848,647 B2 | 12/2017 | Memari et al. | |
| 9,848,648 B2 | 12/2017 | Memari et al. | |
| 9,883,697 B2 | 2/2018 | Memari et al. | |
| 9,955,736 B2 | 5/2018 | Memari et al. | |
| 9,955,737 B2 | 5/2018 | Memari et al. | |
| 9,986,770 B2 | 6/2018 | Memari et al. | |
| 9,993,029 B2 | 6/2018 | Memari et al. | |
| 9,993,030 B2 | 6/2018 | Memari et al. | |
| 9,993,031 B2 | 6/2018 | Memari et al. | |
| 9,993,032 B2 | 6/2018 | Memari et al. | |
| 9,993,033 B2 | 6/2018 | Memari et al. | |
| 9,999,259 B2 | 6/2018 | Memari et al. | |
| 9,999,260 B2 | 6/2018 | Memari et al. | |
| 10,015,995 B2 | 7/2018 | Memari et al. | |
| 10,015,996 B2 | 7/2018 | Memari et al. | |
| 10,021,916 B2 | 7/2018 | Memari et al. | |
| 10,028,536 B2 | 7/2018 | Memari et al. | |
| 10,045,565 B2 | 8/2018 | Memari et al. | |
| 10,045,566 B2 | 8/2018 | Memari et al. | |
| 10,070,662 B2 | 9/2018 | Gorilovsky | |
| 10,081,531 B2 | 9/2018 | Murison et al. | |
| 10,091,839 B2 | 10/2018 | Murison et al. | |
| 10,092,035 B2 | 10/2018 | Memari et al. | |
| 10,099,916 B2 | 10/2018 | Murison et al. | |
| 10,130,119 B2 | 11/2018 | Murison | |
| 10,131,532 B2 | 11/2018 | Murison et al. | |
| 10,136,674 B2 | 11/2018 | Murison et al. | |
| 10,138,113 B2 | 11/2018 | Murison | |
| 10,143,235 B2 | 12/2018 | Memari et al. | |

(Continued)

*Primary Examiner* — Phu H Nguyen
(74) *Attorney, Agent, or Firm* — Birdwell & Janke, LLP

(57) ABSTRACT

An e-cigarette vaporizer device filling system and method. The system and method is particularly adapted for filling sealed vaporizer devices by use of a needle, such as a hypodermic needle, and facilitates separation of the needle from the device after filling.

18 Claims, 7 Drawing Sheets

(56) References Cited

U.S. PATENT DOCUMENTS

| | | |
|---|---|---|
| 10,440,989 B2 | 10/2019 | Gardella et al. |
| 2002/0159915 A1 | 10/2002 | Zelina et al. |
| 2004/0237466 A1 | 12/2004 | Grossman et al. |
| 2006/0005896 A1 | 1/2006 | Till |
| 2006/0011262 A1 | 1/2006 | Stienen |
| 2010/0276034 A1 | 11/2010 | Gonnelli et al. |
| 2012/0167906 A1 | 7/2012 | Gysland |
| 2013/0284192 A1 | 10/2013 | Peleg et al. |
| 2015/0053217 A1 | 2/2015 | Steingraber et al. |
| 2015/0245654 A1 | 9/2015 | Memari et al. |
| 2016/0150824 A1 | 6/2016 | Memari et al. |
| 2017/0121169 A1* | 5/2017 | Dailey .................. B65B 43/54 |

* cited by examiner

E-CIGARETTE VAPORIZER DEVICE FILLING SYSTEM AND METHOD

FIELD OF THE INVENTION

The present invention relates to a system and method for filling vaporizer devices used in electronic or e-cigarettes, with the liquids from which the desired vapors are produced. More specifically, the invention relates to a system and method for filling such devices through seals enclosing the liquid containing chambers therein.

BACKGROUND

Commonly, e-cigarettes consist of a battery, a mouthpiece, and a vaporizing unit having two ends, one of which is removably attached to the battery and the other of which is removably attached to the mouthpiece. The vaporizing unit contains a liquid reservoir which is heated by the battery to produce vapors that are drawn by the user through the mouthpiece, and which is capped with a removable stopper.

It is currently less common but becoming more so that the mouthpiece and vaporizing unit are provided together as a unitary vaporizer device providing for just one user-removable connection to the battery. In this alternative configuration, the removable stopper is replaced with a permanent seal over the liquid reservoir, which must be punctured with a needle to fill the reservoir. This seal is "self-healing" after the needle is removed, a feature that results both because a compliant material is used for the seal and because a sharp needle is used to puncture it. Typically, the needle has the sharpness of a hypodermic needle.

SUMMARY

An e-cigarette vaporizer device filling system and method is disclosed herein.

The filling system and method is particularly adapted for injecting liquid into a vaporizer device that has a sealed opening for receiving the liquid. The method includes providing an injection device and a needle in fluid communication therewith, the needle terminating in a sharp end. The liquid is introduced into the injection device, and the needle is moved over an injection range, relative to the vaporizer device, at least far enough so that the end of the needle punctures the sealed opening of the vaporizer device. Liquid is injected from the injection device through the needle and into the vaporizer device through the punctured, sealed opening after the needle has been moved, and the end of the needle is withdrawn from the vaporizer device after the liquid has been injected. The vaporizer device is maintained substantially stationary during the withdrawing.

Optionally the vaporizer device may also be maintained substantially stationary during the moving and the injecting.

Optionally, the method may include an inherently performed step of self-healing of the sealed opening.

Optionally, the method may include shrouding the end of the hypodermic needle sufficient to prevent finger-tip access thereto over substantially the entirety of the injection range.

The system includes a support framework, an injection device and a needle in fluid communication therewith, the needle terminating in a sharp end, and a guard block. The guard block has a cavity therein for receiving at least a receiving-portion of the vaporizer device. The needle is carried by the support framework so as to allow, under human or machine power and control, for moving the needle over an injection range, at least far enough so that the end of the needle intrudes into the cavity and punctures the sealed opening, injecting liquid from the injection device through the needle and into the vaporizer device through the punctured, sealed opening, and withdrawing the end of the needle from the vaporizer device thereafter. The cavity is capped to maintain the vaporizer device substantially stationary during the withdrawing.

Optionally, the needle may be dimensioned to cooperate with the sealed opening so as to inherently result in self-healing of the sealed opening after said withdrawing.

Optionally, the system may include a shrouding spaced apart from the end of the needle and at least partially surrounding the end of the needle, sufficient to prevent finger-tip access thereto over substantially the entirety of the injection range of the needle.

Optionally, the shrouding may be fixedly disposed relative to the guard block; or more specifically, the shrouding may be fixedly attached to the guard block; or more specifically still, the shrouding may be an integral part of the guard block.

Optionally, the guard block may include one or more tapered surfaces effective to help guide the vaporizer device into a predetermined position relative to the needle as the vaporizer device is received by the cavity; and/or one or more tapered surfaces effective to help guide the needle into a predetermined position relative to the vaporizer device as the needle is received by the cavity.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DETAILED DESCRIPTION OF PREFERRED EMBODIMENTS

Figure 1:
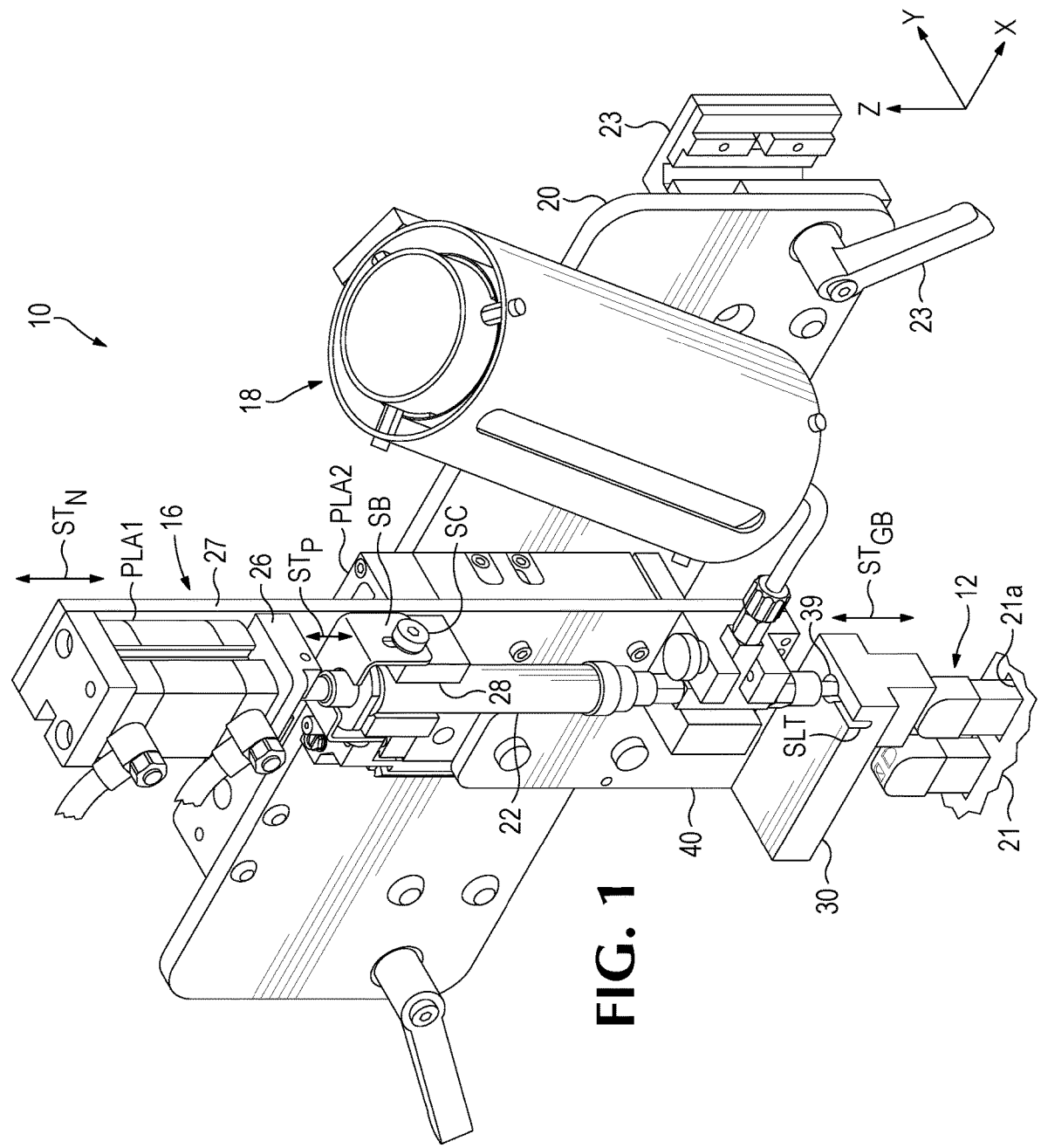
FIG. 1 is an isometric view of a filling apparatus according to the present invention for filling an e-cigarette vaporizer device.

FIG. 1 shows a filling system 10 according to the present invention, for filling a vaporizer device 12 with a liquid, typically an oil, which is ultimately to become vaporized in the vaporizer device for inhalation by a user. Such oils are known as e-liquids. CBD oil, Rick Simpson oil (RSO), Rosin oil, Live Resin oil, Distillate oil (a distilled version of a cannabis extract), High Terpene Full Spectrum Extract oil (HTFSE), and High Cannabinoid Full Spectrum Extract oil (HCFSE) are examples of such e-liquids. Hereinafter, the term "liquid" will be used to refer to any type of e-liquid that is or can be used in an c-cigarette.

Figure 2:
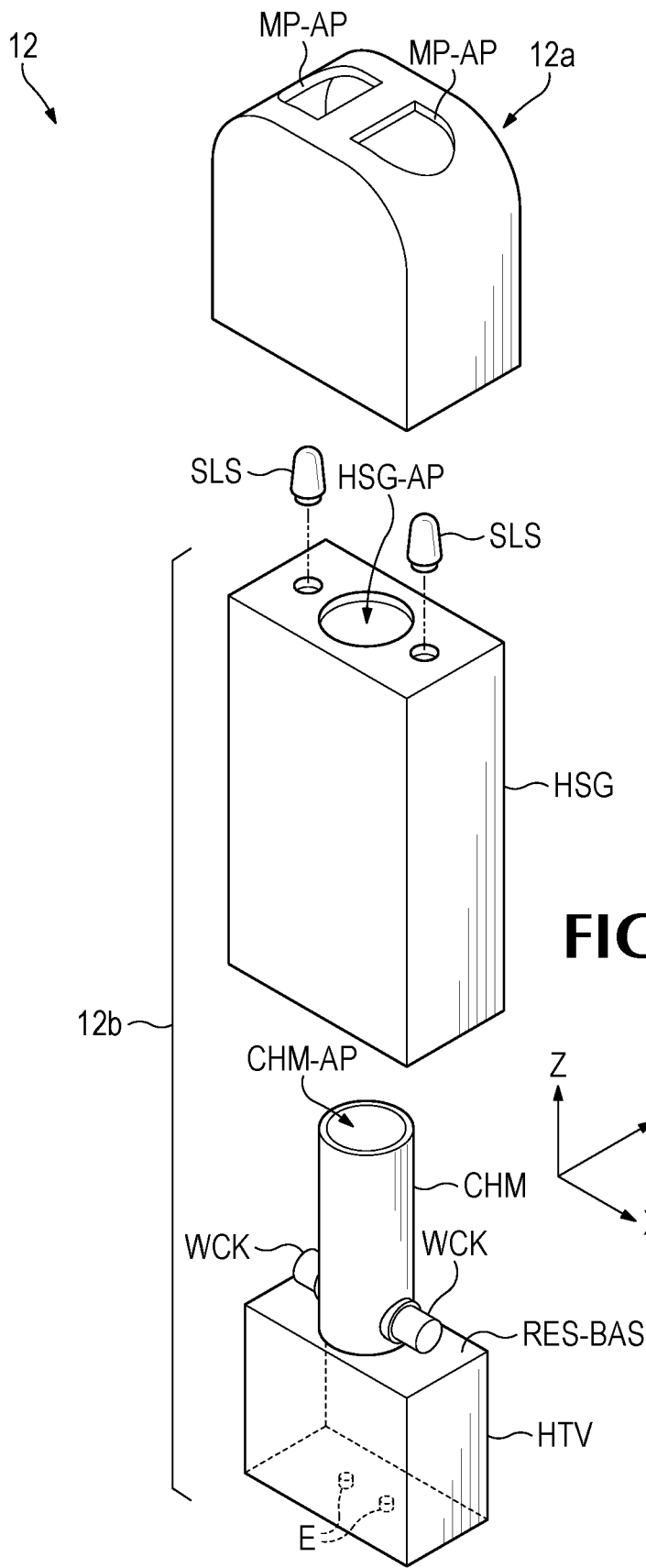
FIG. 2 is an exploded view of a generic vaporizer device as shown in FIG. 1.
Figure 3:
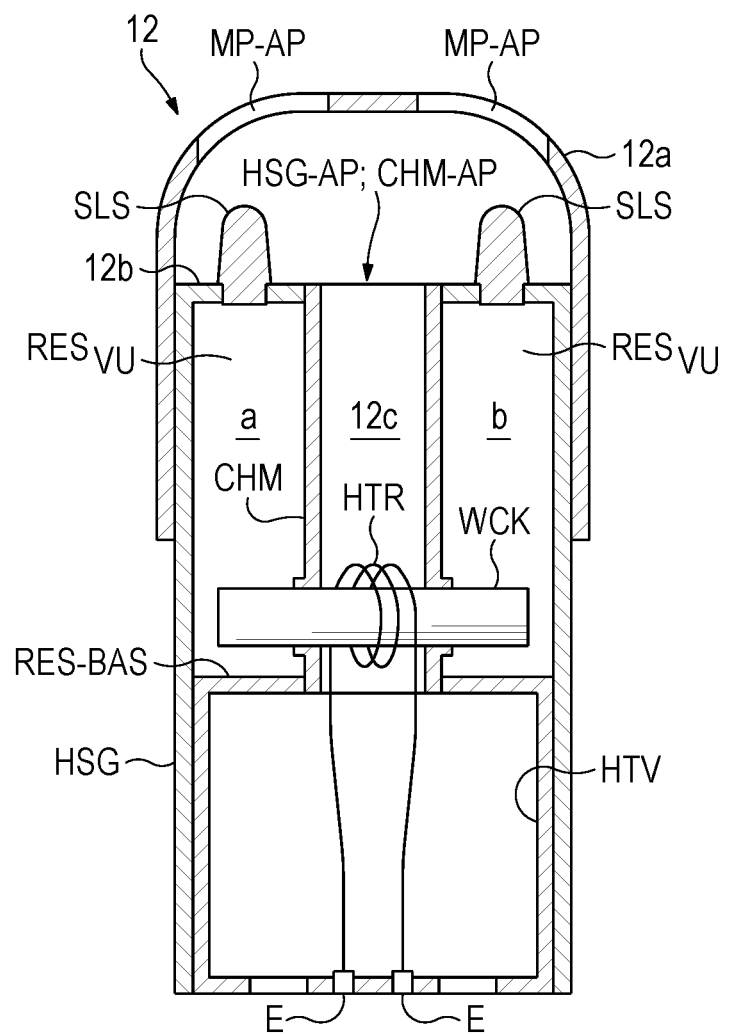
FIG. 3 is a cross-sectional front elevation view of a generic prior art vaporizer unit.

A generic vaporizer device 12 is shown in more detail in FIGS. 2 and 3. As shown in FIG. 2, the device 12 has a mouthpiece 12a, and a vaporizer unit 12b. The specific vaporizer device 12 does not have a battery; it is intended to be removably connected to a battery possessed by the user, at electrical contacts "E." However the filling system 10 could just as well be used for vaporizer devices that include batteries, i.e., vaporizer devices that include all three of the essential parts of an e-cigarette, a mouthpiece, a vaporizing unit, and a battery unit, together in a single or unitary device.

Figure 4:
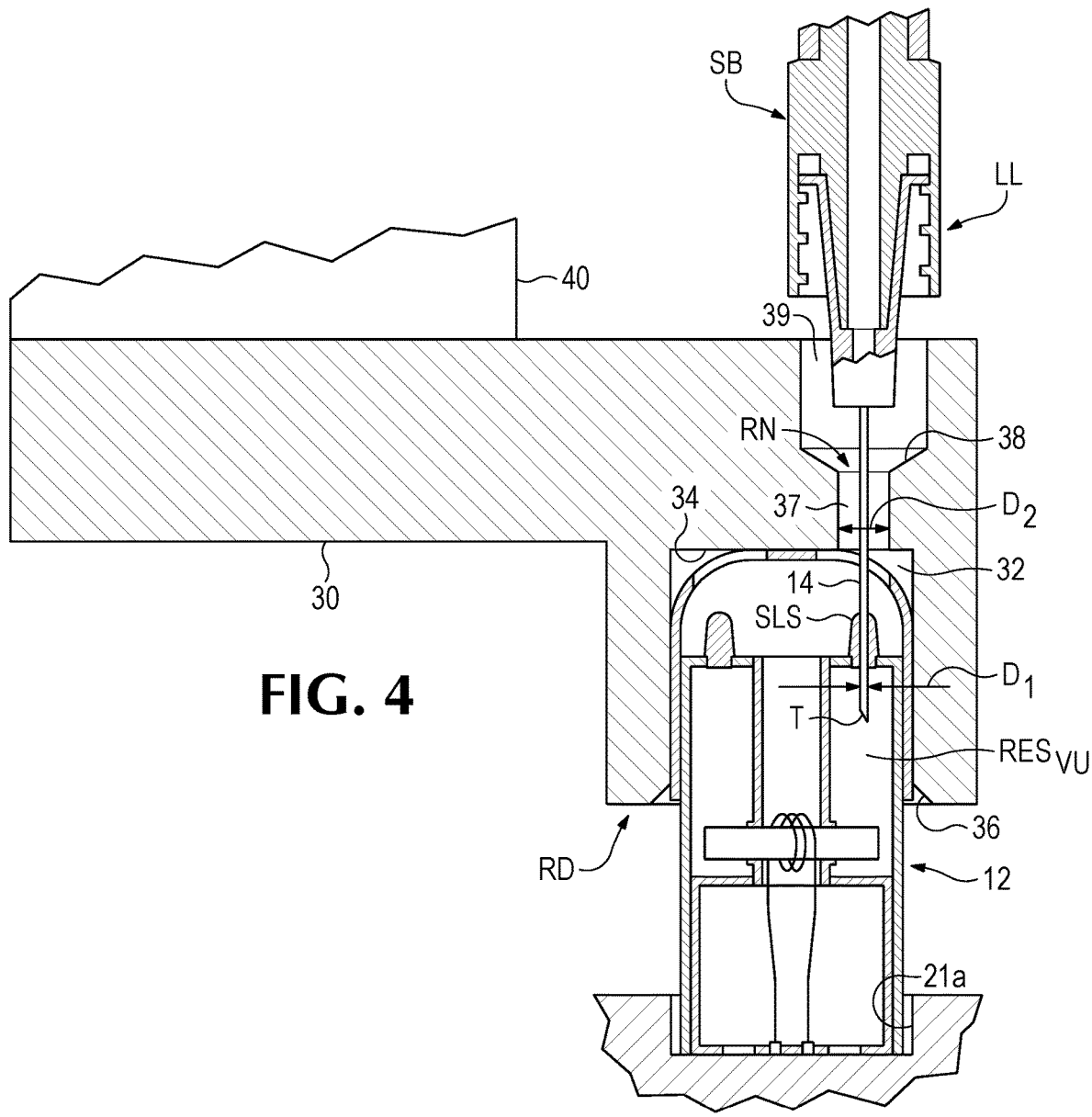
FIG. 4 is a fragmented cross-sectional front elevation view of a guard block according to the present invention, for injecting e-liquid into the vaporizer unit of FIG. 3.

Two of the vaporizer devices 12 are shown in FIG. 1 supported on a table 21 (shown fragmented), which could be an X-Y positionable table such as that described in U.S. Pat. No. 10,440,989, the disclosure of which is incorporated by reference herein in its entirety. As can be seen in FIGS. 1 and 4, the table would typically have wells 21a for loosely receiving bottom-most oriented portions of the vaporizer devices. However, the vaporizer devices 12 could be supported on any suitable support surface, with any suitable holder or fixture, in any orientation, as desired.

With particular reference to FIG. 3, the vaporizer unit 12b has a heating unit "HTU" that encloses a resistive heating element "HTR" which is electrically connected to the electrical contacts E. A top of the heating unit HTU defines a vaporizer unit reservoir base "RES-BAS" for a vaporizer unit reservoir "$RES_{VU}$" enclosed by the following elements: the vaporizer unit reservoir base, a housing "HSG" of the vaporizer unit, and the exterior surface of a chimney "CHM." The width of the reservoir base (measured along the dimension "Y" in FIG. 2) exceeds the diameter of the chimney so liquid can flow, under pressure of gravity, between two laterally (measured along the dimension "X" in FIG. 2) spaced apart sides "a" and "b" of the reservoir. A wick "WCK" extends into the vaporizer unit reservoir $RES_{VU}$ to conduct liquid by capillary attraction therefrom into an interior 12c of the chimney. The liquid reaching the interior of the chimney may be heated by the heater HTR and thereby vaporized, to travel by convection up the interior of the chimney, thence to exit the chimney and housing through respective, and in this example coaxially coincident, chimney and housing apertures "CHM-AP" and "HSG-AP," and thence to exit the device through one or more (two or shown) mouthpiece apertures "MP-AP."

The vaporizer device 12 as shown is intended to be representative of commercially available units. Some illustrative examples of such units are: the CCell "Liquid9" cartridge, manufactured by Shenzhen Smoore Technology Limited, of Kowloon, Hong Kong and marketed by Jupiter Research of Phoenix Ariz.; the Pax "Era" Pod, manufactured and marketed by Pax Labs, of San Francisco, Calif.; and the Gpen "Nova" Vaporizer, manufactured and marketed by Grenco Science, Inc., of Los Angeles, Calif.

The salient feature of the vaporizer device 12 for purposes of the present invention is the provision of permanent seals "SLS" that plug the vaporizer unit reservoir $RES_{VU}$. These seals must be punctured by an injecting needle to introduce oil into the vaporizer unit reservoir, and they must "self-heal" after the needle is withdrawn to prevent oil from leaking out of the vaporizer unit reservoir. This feature will be discussed further below. Although the seals SLS are shown in FIG. 2 exploded from the housing HSG, it is to be understood that in empty vaporizer units 12 as manufactured to be ready for filling, the seals are sealed to the housing.

Returning to FIG. 1, the filling system 10 includes a liquid injection mechanism 16 and a filling reservoir 18, which provides a reservoir of heated liquid for delivery to the liquid injection mechanism. An example of the filling reservoir 18 and a provision for heating the liquid therein is shown and described in the '989 patent. Heating the liquid allows it to flow through the system 10 with greater speed, which increases throughput, and/or with less force, which reduces the mechanical requirements.

The liquid injection mechanism 16 may be mounted on a gantry 20 which may be slidably mounted to upright parallel support posts for elevation adjustment along the Z axis (see the indicated X, Y, Z coordinate axes indicated) relative to an X-Y table 21 (such as that shown and described in the '989 patent), or other structure that may be used to support one or more of the vaporizer units 12. Standard locking means 23 may be provided for locking the gantry at a desired elevation. This will allow for filling vaporizer units of varying heights. No such structure or height adjustment is required, however.

Figure 5:
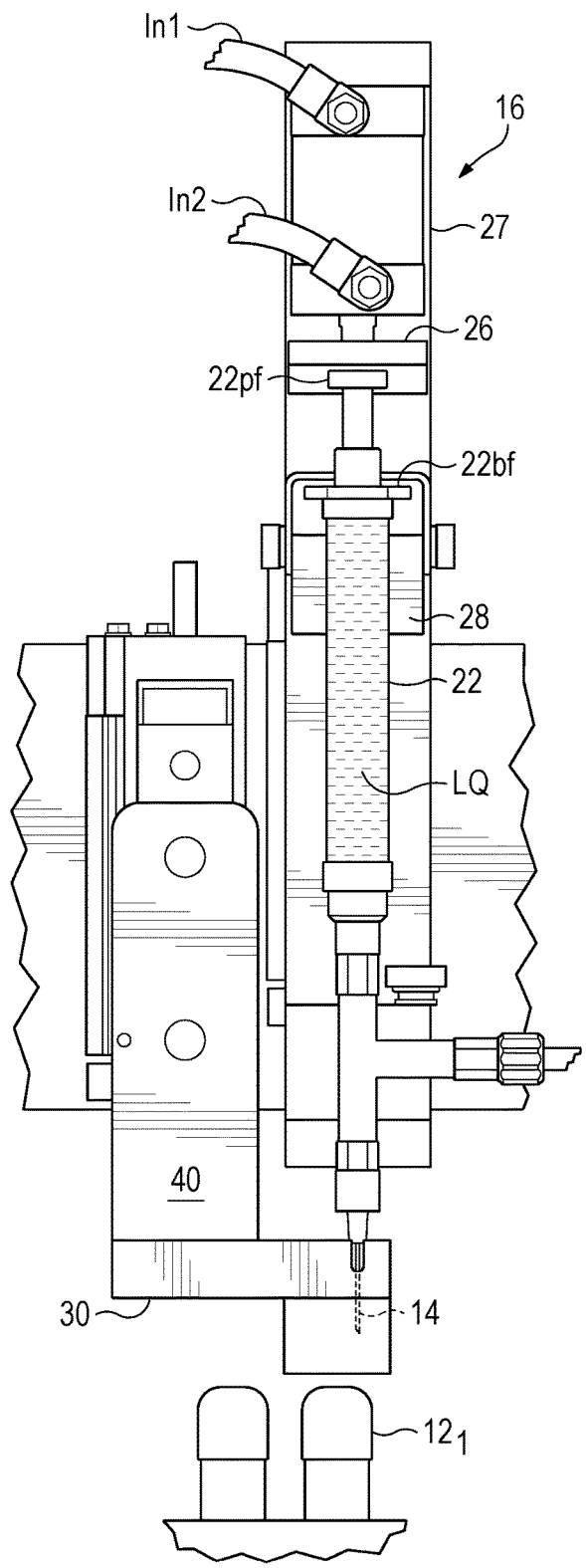
FIG. 5 is a fragmented front elevation view of the filling apparatus of FIG. 1 in a first, "ready" configuration for filling a first instance of the vaporizer unit of FIG. 3.

With reference to FIGS. 1 and 5, the liquid injection mechanism 16 is adapted to operate an injection device or syringe 22 in the manner that it would normally be operated by a human user, and provide for two independent reciprocating motions along an axis of "stroke" which, as shown, may be parallel to the Z axis.

To accomplish this, the liquid injection mechanism 16 may be provided as described in the '989 patent and include a receiver 26 for receiving a plunger flange "22pf" of the syringe 22, and a receiver 28 for receiving a body flange "22bf" of the syringe 22. One of these components may have a fixed recess shaped to fit the corresponding flange, while the other may have an adjustably sized recess, adjustable in the direction of stroke, to facilitate installation of the liquid injection syringe 22 in the liquid injection mechanism 16. In the embodiment shown, the receiver 28 has the fixed recess and the receiver 26 has the adjustable recess, provided by a slotted bracket "SB" and screws "SC" threaded into a body portion of the receiver 58.

The receivers 26 and 28 may both be mounted on a carriage 27. The receivers are provided so that one of the receivers can translate relative to the other, parallel to directions of stroke "$ST_P$," again, to provide for operating the syringe in the manner that it would normally be operated by a human user. In the embodiment shown, the receiver 26 moves while the receiver 28 remains fixed relative to the carriage 27. If the spacing between the two receivers is increased, the syringe is enabled to draw liquid from the liquid reservoir 18, and if the spacing between the two receivers is decreased, the syringe is enabled to expel or inject the liquid through and out the end of an injecting needle 14 (not visible in FIG. 1; see FIG. 4).

The carriage 27 can also be translated, parallel to directions of stroke "$ST_N$," carrying the syringe 22 and the receivers 26 and 28 together as a group or unit, to provide for inserting the needle 14 of the syringe into a selected vaporizer unit 12.

The directions of stroke $ST_P$ and $ST_N$ are typically though not necessarily congruent, and are for reference purposes shown parallel to the Z axis.

These motions may be pneumatically powered, by use of standard pneumatic linear actuators. Shown is a first pneumatic linear actuator PLA1, for moving the receiver 26 relative to the receiver 28, and a second pneumatic linear actuator PLA2, for moving the carriage 27. Both pneumatic actuators would be provided with a source of compressed air; as shown for the actuator PLA1, such actuators have, generally, two air inputs "In1" and "In2."

As will be readily appreciated by persons of ordinary mechanical skill, the filling system 10 could be adapted so that one or both of the motions described above are powered by alternative sources, including by hand such as in the manner of a drill press.

A guard block 30 is also provided according to the invention, on a carriage 40 that may be powered in the same manner as described above for the carriage 27, to reciprocate the guard block in directions of stroke "$ST_{GB}$" that would typically, though not necessarily, be parallel to the directions of stroke $ST_P$ and $ST_N$.

The guard block 30 can be seen in more detail in FIG. 4. It has a cavity 32 sized to receive an upper-most oriented portion of a vaporizer unit 12; a cap 34 that constrains movement of the vaporizer device 12; a first internal surface 36 at a vaporizer device-receiving opening "RD" that is angled or tapered relative to the direction of stroke $ST_P$ of the guard block; a set of needle-receiving apertures 37 and 39 for receiving the injection needle 14 therethrough; and a second internal surface 38 between the needle-receiving apertures, defining a needle-guiding opening "RN," that is angled or tapered relative to the direction of stroke of the guard block. Referring back to FIG. 1, the guard block 30 also has a slot "SLT" that joins the needle-receiving aperture 39.

FIGS. 5-9 show an exemplary sequence of operation of the filling system 10.

First, in FIG. 5, an empty vaporizer unit $12_1$, which is empty and ready to be filled with liquid, is positioned directly underneath the liquid injection mechanism 16. The liquid injection syringe 22 has been filled with liquid "LQ" from the filling reservoir 18, such as described in the '989 patent. The liquid injection mechanism is aligned with the vaporizer unit so that the injection needle 14 is positioned over a selected one of the seals SLS (not visible in FIG. 5; see FIG. 4) of the vaporizer unit. The carriage 27 and therefore the needle 14 is in a retracted position. The guard block 30 is also in a retracted position in which the retracted injection needle 14 extends down through the needle-receiving apertures 39 and 37, and into the cavity 32, so that a human user of the filling system 10 will be protected from inadvertent contact with the end of the needle.

Figure 6:
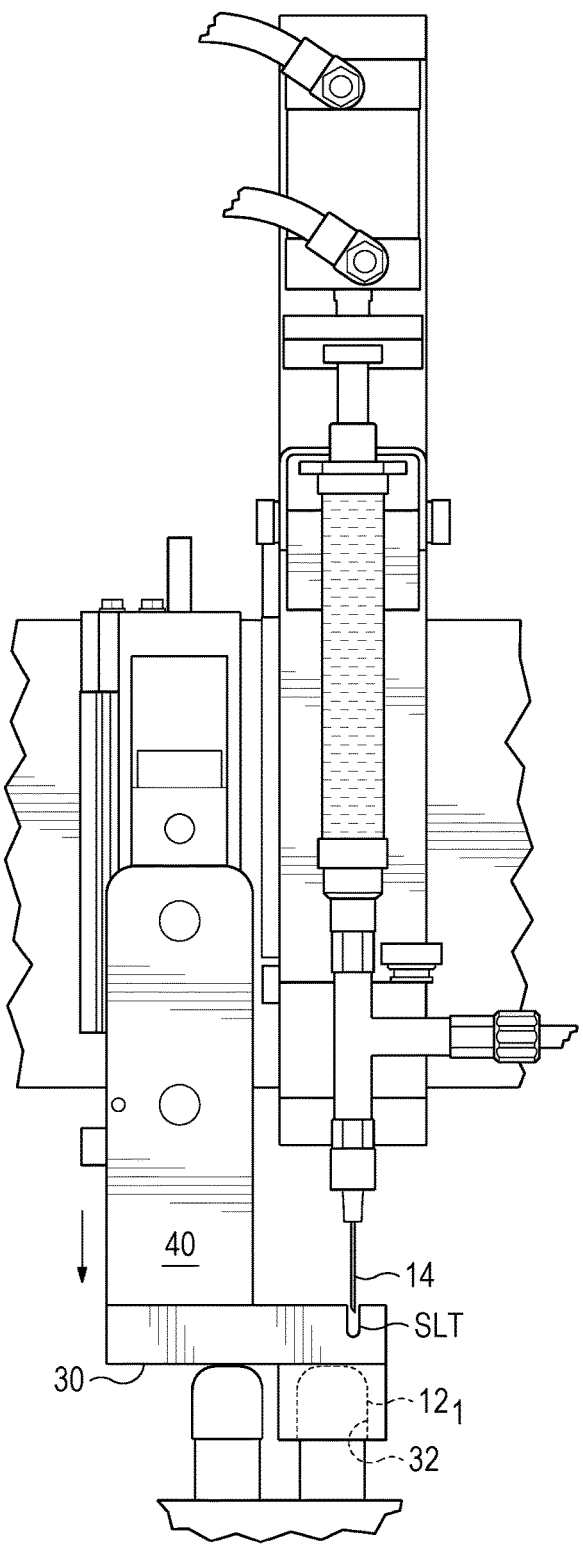
FIG. 6 shows the apparatus of FIG. 5 in a second configuration in which the guard block of FIG. 1 has been extended.

Next, in FIG. 6, the guard block 30 has been translated downwardly, i.e., in the downward direction of the stroke $ST_{GB}$ (see arrow), to reach an extended position in which the upper-most portion of the vaporizer unit $12_1$ (shown in dashed lines) is received in the cavity 32. By this extending motion, the guard block withdraws from the retracted injection needle 14 so that the tip "T" of the needle is no longer in the cavity 32. But the guard block is preferably not withdrawn so far from the needle that its tip is exposed; the tip of the needle preferably remains sufficiently shrouded by at least one of the needle-receiving apertures 37 and 39 that a human user of the filling system 10 will be protected from inadvertent contact with the tip of the needle.

Figure 7:
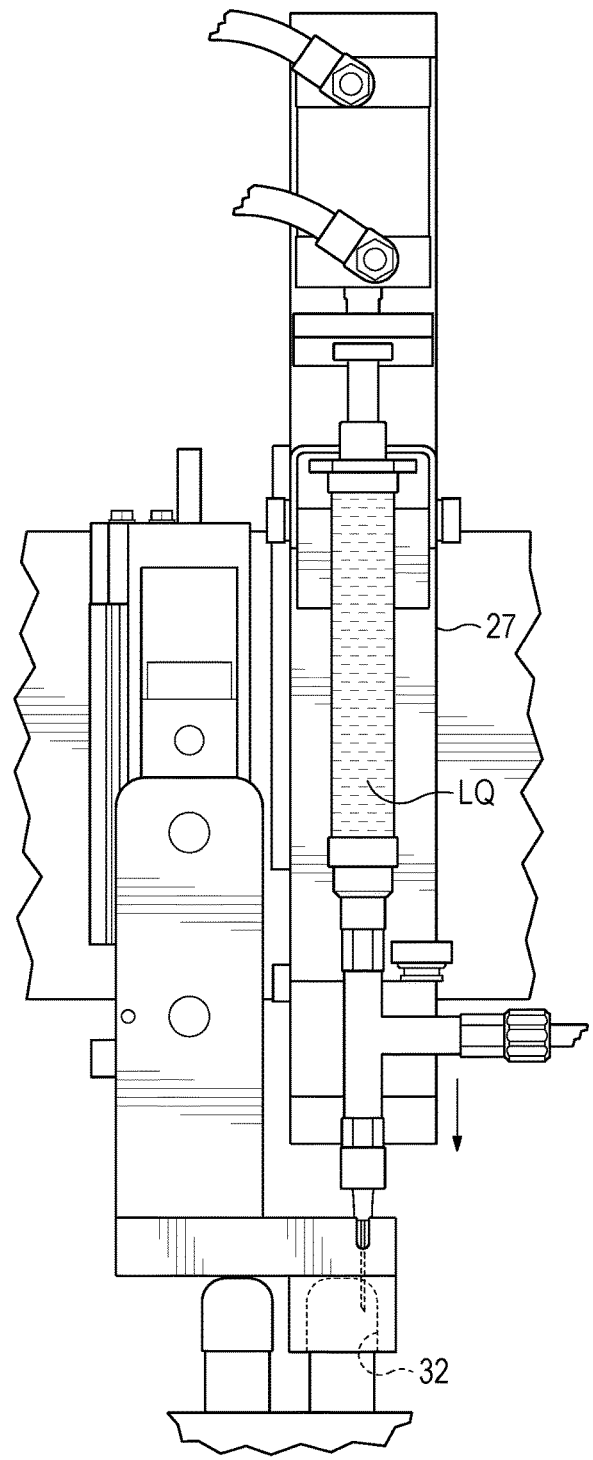
FIG. 7 shows the apparatus of FIG. 5 in a third configuration in which the needle of FIG. 1 has been extended.

Next, in FIG. 7, the carriage 27 and therefore the injection needle 14 has been translated downwardly, i.e., in the downward direction of the stroke $ST_N$ (see arrow), to reach an extended position in which the needle extends into the cavity 32 of the extended guard block 30 as shown in FIG. 4. Staying with FIG. 4, this motion causes the tip T of the needle 14 to puncture the seal SLS and intrude the vaporizer unit reservoir $RES_{VU}$.

Figure 8:
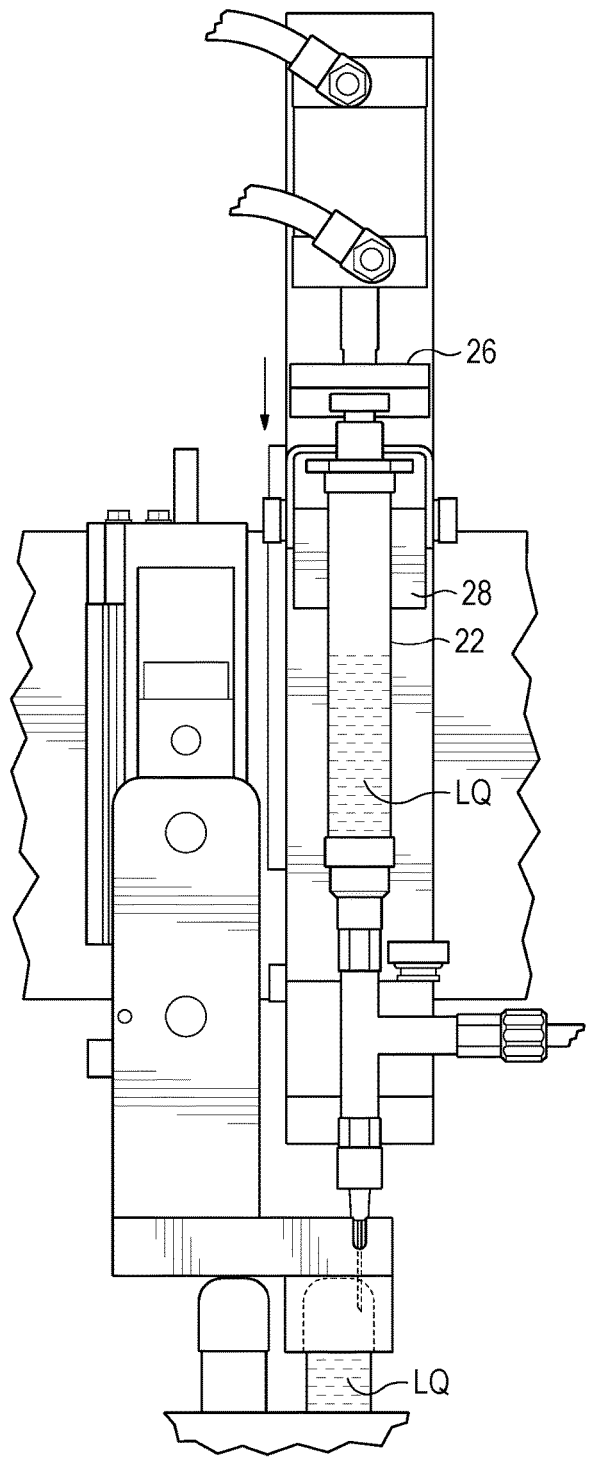
FIG. 8 shows the apparatus of FIG. 5 in a fourth configuration in which a plunger of the syringe shown in FIG. 1 is depressed.

Next, in FIG. 8, the receiver 26 is translated downwardly, i.e., in the downward direction of the stroke $ST_P$ (see arrow), relative to the receiver 28, to depress the plunger and thereby expel some of the liquid LQ from the syringe 22 into vaporizer unit reservoir $RES_{VU}$. The amount of liquid expelled from the syringe can be controlled by controlling the amount of the translation of the receiver 26.

Not shown are the reverse motions: retracting the receiver 26 in the upward direction of the stroke $ST_P$ and thereby reversing the motion shown in FIG. 8; retracting the carriage 27 and therefore the injection needle 14 in the upward direction of the stroke $ST_N$, and thereby reversing the motion shown in FIG. 7; and retracting the guard block 30 in the upward direction of the stroke $ST_{GB}$ and thereby reversing the motion of FIG. 6; to return the filling system to the "ready" configuration shown in FIG. 5.

Figure 9:
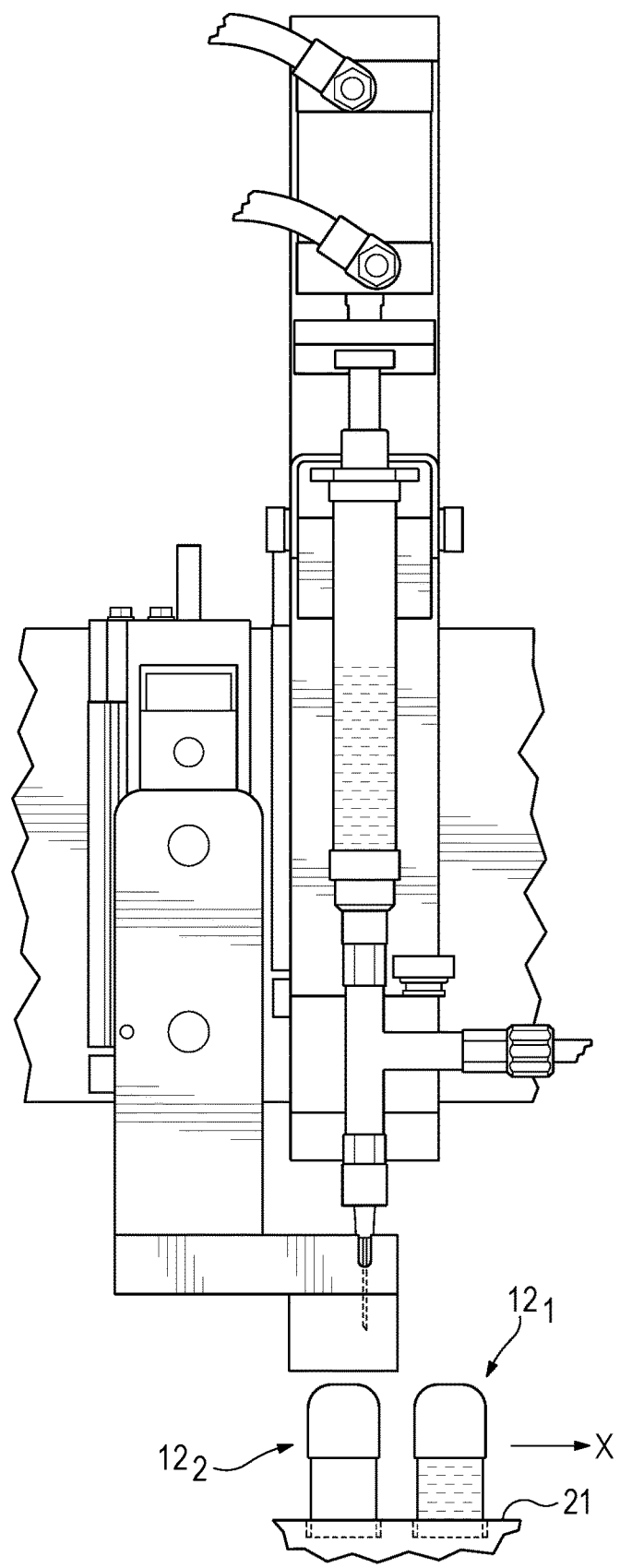
FIG. 9 shows the apparatus of FIG. 5 in the same "ready" configuration for filling a second instance of the vaporizer unit of FIG. 3.

FIG. 9 shows one more motion, i.e., translation of the table 21 (see arrow) to move a "next" vaporizer unit $12_2$ to be filled, into the position previously occupied by the vaporizer unit $12_1$ in FIGS. 5-8.

Returning to FIG. 4 and as noted previously, the guard block 30 has a cap 34. This cap performs an important function of holding or retaining the vaporizing device in place against pulling force that is exerted on the vaporing device as a consequence of withdrawing the injection needle from the seal SLS. The cap 34 is located at an uppermost portion of the cavity 32, of closest approach to the needle 14 when the needle is in its retracted position as in FIGS. 5 and 6.

Further as noted previously, the guard block 30 has a first internal surface 36, at a vaporizer device-receiving opening "RD" of the guard block, at the entrance of the cavity 32, which is angled or "tapered" relative to the direction of stroke $ST_P$ of the guard block. This first tapered surface performs an important function of guiding the vaporizing device into registration with the needle 14, as the guard block 30 is brought down upon the vaporizing device.

Still further as noted previously, the guard block 30 has a second internal surface 38 at a needle-guiding opening "RN" of the guard block, which is tapered relative to the direction of stroke $ST_P$ of the guard block. This second tapered surface may be used to guide the needle into registration with the cavity 32.

It has been found to be preferable to provide that the needle-receiving aperture 37 is a cylindrical hole, preferably having a diameter "$D_2$" that is greater than, but no more than +0.010 inches greater than, the diameter "$D_1$" of the needle 14. It has also been found to be preferable for the needle-receiving aperture 39 to be a cylindrical hole, which would of course have a larger diameter than the diameter $D_2$ given the diameter-reduction provided by the tapered surface(s) 38 of the needle-guiding opening RN.

Returning to FIG. 1 and as noted previously, the guard block 30 also has a slot "SLT" that joins the needle-receiving aperture 39. This slot allows for retaining the protective features of the guard block described above, at the same time as allowing for removing and installing the syringe 22 when the filling system 10 is in the "guard block extended/needle retracted" configuration shown in FIG. 6.

As noted previously, the seals SLS of the vaporizer units are self-healing, which means they will remain liquid-tight under standard atmospheric pressure after first having been punctured by the injecting needle and after the needle has been withdrawn from the vaporizer unit, as is the case for the vaporizer unit $12_1$ in FIG. 9.

With reference to FIG. 4, this self-healing feature presumes dimensional characteristics of the needle, namely its width, typically represented by a diameter "$D_1$" (FIG. 4) if the needle is cylindrical, and the sharpness of the tip T, provided to function in conjunction with the material properties of the sealing material or materials employed for sealing the opening of the vaporizer device, so that puncturing the seal with the needle will not rupture the seal.

The needles employed in hypodermic syringes have been found to be well suited to this purpose. Examples are the BD "Precision Glide" Needles, #305195 and #305199, manufactured and marketed by Becton, Dickinson and Company, of Franklin Lakes, N.J. Such needles are typically removably connected to syringe bodies, such as the portion of the syringe 22 referenced as "SB" in FIG. 4, by use of a very coarsely threaded "Luer Lock" an example of which is referenced as "LL" in the same Figure. A "slip tip" is a related type of connector, also used for connecting hypodermic needles to hypodermic syringes. The Leur Lock and slip tip connections allow for replacing worn needles without need for replacing the entire syringe, and for installing different sizes or types of needles on the same syringe body.

The guard block 30 may be formed either as a unitary whole or as an assembly of joined parts, as desired.

The "injection range" of a needle is the difference in of the tip of the needle in its retracted position (shown for the needle 14 in FIGS. 5, 6 and 9), and the elevation of the tip of the needle in its extended position (shown for the needle 14 in FIGS. 7 and 8).

The tapered surfaces need not be planar as shown for the surfaces 36 and 38 shown in FIG. 4. They could be curved and still be tapered and perform the desired funneling function. To perform this function however, they must taper in specific directions. The surface 36 must taper so as to narrow the opening of the cavity 32 with increasing proximity to the needle (the positive Z direction for the filling system oriented as shown in FIG. 1), to funnel the vaporizer device toward the needle. And the surface 38 must taper so as to narrow the opening established by the needle-receiving aperture 39 with increasing proximity to the cavity 32, to funnel the needle toward the cavity. The term "tapered surface" as used herein will be understood to imply these specific directionalities.

As will be readily apparent to a person of ordinary skill, an electrical controller could be provided for controlling the operations shown in FIGS. 5-9, which could be an adaptation of the controller described in the '989 patent. However, as noted previously, all of the motions described could be provided and controlled by a user of the device, for example, by the use of foot controlled pneumatic switches for switching air inlet lines to the pneumatic actuators on and off in any desired sequence, or they could be controlled by a pneumatic controller employing pneumatic logic switching devices.

While the filling system 10 is adapted specifically for use in filling vaporizer devices that have liquid-tight seals, the seals need not be liquid tight, they could be removable in the manner of a stopper, and the system could be used for filling other kinds of devices.

While the injection device has been shown and described as a syringe, other devices could be used to inject liquid according to the invention. For example, a peristaltic pump could be used as an injection device, or a hydraulic actuator could be used in reverse; by providing the liquid to be injected to the input hydraulic line of the hydraulic actuator, and manipulating the actuator (such as by use of the same pneumatic linear actuator PLA1 discussed above) to expel liquid from the outlet hydraulic line of the hydraulic actuator. Both of these alternatives would allow for injecting controlled amounts of liquid. It is likely that a needle with a Leur Lock connector can be coupled to the connectors of an alternative injection device with a commercially available adaptor; but if not, it should be readily apparent to persons of ordinary mechanical skill how to make the connections, as well as how to modify the carriage to carry the injection device. Moreover, if an alternative injecting device, such as a hydraulic actuator or a peristaltic pump, is employed, the needle need not be directly connected to the injection device. Fluid communication between the needle and injection device could be made through flexible hoses or tubing that allow for mounting the injection device remotely from the carriage 27, so that the carriage could be used merely to move the needle, rather than to move both the needle and the injection device as in the embodiment shown.

The vaporizer device 12 as shown is provided to be filled through the top of the device, but vaporizer devices may be currently provided, or developed in the future, to be filled from the bottom, or from a side, or from some other direction. The only impact of this potential difference in filling orientation would be to the manner the vaporizer device is held for filling, such as the shape and size of the wells 21a in the tray 21. How the vaporizer device is oriented for filling is not pertinent to the invention.

So it is to be understood that, while a specific e-cigarette vaporizer device filling system and method has been shown and described as preferred, other configurations and methods could be utilized, in addition to those already mentioned, without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A system for injecting liquid into a vaporizer device, the vaporizer device having an upper portion with a sealed opening for receiving the liquid, the system comprising:
   an injection device and a needle connected thereto, the needle terminating in a needle tip;
   an injection device carriage;
   a guard block;
   a guard block carriage; and
   a support framework for supporting the injection device carriage and the guard block carriage, the guard block having opposed upper and lower portions, the lower portion of the guard block having a cavity therein, and the guard block having an aperture extending through the guard block from a top surface at the upper portion of the guard block to an opening into the cavity, wherein the injection device carriage allows for moving the needle over an injection range along an axis of stroke, over which the needle tip can be extended through the aperture and into the cavity, for puncturing the sealed opening of the vaporizer device and injecting liquid from the injection device through the needle tip into the vaporizer device through the punctured opening, and withdrawn from the vaporizer device after said injecting, wherein the guard block carriage allows for moving the guard block parallel to the axis of stroke, in a first direction for placing the cavity over the vaporizer device and thereby receiving at least the upper portion of the vaporizer device in the cavity, and a second direction opposite the first direction for freeing the vaporizer device from the cavity.

2. The system of claim 1, wherein the aperture, at the opening into the cavity, is narrower, in all directions perpendicular to the axis of stroke, than the cavity itself.

3. The system of claim 2, the lower portion of the guard block defining a vaporizer device receiving opening into the cavity, wherein the vaporizer device receiving opening includes one or more tapered surfaces effective to help guide the vaporizer device into a predetermined position relative to the needle in the cavity as the cavity receives the vaporizer device.

4. The system of claim 2, wherein the aperture, somewhere between the top surface of the guard block and the opening, has one or more tapered surface effective to help guide the needle into a predetermined position relative to the opening.

5. The system of claim 4, the lower portion of the guard block defining a vaporizer device receiving opening into the cavity, wherein the vaporizer device receiving opening includes one or more tapered surfaces effective to help guide the vaporizer device into a predetermined position relative to the needle in the cavity as the cavity receives the vaporizer device.

6. The system of claim 1, the lower portion of the guard block defining a vaporizer device receiving opening into the cavity, wherein the vaporizer device receiving opening includes one or more tapered surfaces effective to help guide the vaporizer device into a predetermined position relative to the needle in the cavity as the cavity receives the vaporizer device.

7. The system of claim 1, wherein the aperture, somewhere between the top surface of the guard block and the opening, has one or more tapered surface effective to help guide the needle into a predetermined position relative to the opening.

8. The system of claim 7, the lower portion of the guard block defining a vaporizer device receiving opening into the cavity, wherein the vaporizer device receiving opening includes one or more tapered surfaces effective to help guide the vaporizer device into a predetermined position relative to the needle in the cavity as the cavity receives the vaporizer device.

9. The system of claim 1, wherein the needle is dimensioned to cooperate with the sealed opening so as to inherently result in self-healing of the sealed opening after the needle tip is withdrawn from the vaporizer device.

10. The system of claim 1, including a shrouding spaced apart from of the needle tip and at least partially surrounding the needle tip, sufficient to prevent finger-tip access thereto over substantially the entirety of the injection range of the needle.

11. The system of claim 10, wherein the shrouding is part of the guard block.

12. A system for injecting liquid into a vaporizer device, the vaporizer device having an upper portion with a sealed opening for receiving the liquid, the system comprising:
an injection device and a needle connected thereto, the needle terminating in a needle tip;
an injection device carriage;
a guard block;
and a support framework for supporting the injection device carriage and the guard block, the guard block having opposed upper and lower portions, the lower portion of the guard block having a cavity therein for receiving at least the upper portion of the vaporizer device, and the guard block having an aperture extending through the guard block from a surface at the upper portion of the guard block to an opening into the cavity, wherein the injection device carriage allows for moving the needle over an injection range along an axis of stroke, over which the needle tip can be extended through the aperture and into the cavity, for puncturing the sealed opening of the vaporizer device and injecting liquid from the injection device through the needle tip into the vaporizer device through the punctured opening, and withdrawn from the vaporizer device after said injecting, wherein the aperture, at the opening into the cavity, is narrower, in all directions perpendicular to the axis of stroke, than the cavity itself.

13. The system of claim 12, the lower portion of the guard block defining a vaporizer device receiving opening into the cavity, wherein the vaporizer device receiving opening includes one or more tapered surfaces effective to help guide the vaporizer device into a predetermined position relative to the needle in the cavity as the cavity receives the vaporizer device.

14. The system of claim 12, wherein the aperture, somewhere between the surface and the opening, has one or more tapered surface effective to help guide the needle into a predetermined position relative to the opening.

15. The system of claim 14, the lower portion of the guard block defining a vaporizer device receiving opening into the cavity, wherein the vaporizer device receiving opening includes one or more tapered surfaces effective to help guide the vaporizer device into a predetermined position relative to the needle in the cavity as the cavity receives the vaporizer device.

16. The system of claim 12, wherein the needle is dimensioned to cooperate with the sealed opening so as to inherently result in self-healing of the sealed opening after the needle tip is withdrawn from the vaporizer device.

17. The system of claim 12, including a shrouding spaced apart from the needle tip and at least partially surrounding the needle tip, sufficient to prevent finger-tip access thereto over substantially the entirety of the injection range of the needle.

18. The system of claim 17, wherein the shrouding is part of the guard block.

* * * * *